US007225813B2

(12) United States Patent
Easter

(10) Patent No.: US 7,225,813 B2
(45) Date of Patent: Jun. 5, 2007

(54) RIB FRACTURE SCORE AND PROTOCOL

(75) Inventor: Anna L. Easter, Little Rock, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 922 days.

(21) Appl. No.: 10/630,046

(22) Filed: Jul. 30, 2003

(65) Prior Publication Data

US 2004/0035434 A1 Feb. 26, 2004

Related U.S. Application Data

(60) Provisional application No. 60/405,579, filed on Aug. 23, 2002.

(51) Int. Cl.
*A61B 5/00* (2006.01)
*A61B 19/00* (2006.01)

(52) U.S. Cl. ...................................... 128/898; 600/300

(58) Field of Classification Search ................ 600/300; 128/897, 898, 920, 925; 705/2, 3
See application file for complete search history.

(56) References Cited

U.S. PATENT DOCUMENTS

| 4,839,822 | A | | 6/1989 | Dormond et al. |
| 5,315,505 | A | | 5/1994 | Pratt et al. |
| 5,672,154 | A | | 9/1997 | Sillen et al. |
| 5,692,500 | A | | 12/1997 | Gaston-Johansson |
| 5,826,585 | A | | 10/1998 | Franssen et al. |
| 5,848,594 | A | * | 12/1998 | Matheson ................... 128/898 |
| 5,908,383 | A | | 6/1999 | Brynjestad |
| 6,014,631 | A | | 1/2000 | Teagarden et al. |
| 6,024,699 | A | | 2/2000 | Surwit et al. |
| 6,066,092 | A | | 5/2000 | Cady et al. |
| 6,186,145 | B1 | * | 2/2001 | Brown ....................... 128/897 |
| 6,190,872 | B1 | | 2/2001 | Slotman |
| 6,322,503 | B1 | | 11/2001 | Sparhawk, Jr. |
| 6,529,195 | B1 | | 3/2003 | Eberlein |

OTHER PUBLICATIONS

Atrium, Clinical Update for the Proffessional Nurse, Managing Multiple Rib Fractures, Sep. 2001, 2 pages.*
Easter, Anna, Management of Patients with Multiple Rib Fractures, American Journal of Critical Care, vol. 10, No. 5, Sep. 2001, pp. 320-327.

(Continued)

Primary Examiner—Samuel G. Gilbert
(74) Attorney, Agent, or Firm—Ray F. Cox, Jr.

(57) ABSTRACT

Multiple rib fractures in trauma patients are associated with significant morbidity and mortality. Delayed morbidity for patients with rib fractures is often a result of hypoventilation leading to atelectasis, pneumonia and respiratory failure. Pain management was first recognized as an important factor in preventing complications in these patients. Later, management of the respiratory system became more widely recognized as a major factor in, patients' care. It is now known that patients with multiple rib fractures benefit most from adequate pain control, rapid mobilization, and meticulous respiratory care to prevent complications. A rib fracture score and protocol based on a synthesis of the existing literature is developed. The protocol is directed to decisions about rapid mobilization, respiratory support, and pain management interventions to decrease the length of patients' stay in intensive care units.

6 Claims, 2 Drawing Sheets

OTHER PUBLICATIONS

Honick, D., et al., Fractures, Rib, online serial, eMed J, http://www.emedicine.com/emerg/topic204.htm, Jul. 17, 2001, 11 pages.

Gabram, S., et al., Clinical Management of Blunt Trauma Patients with Unilateral Rib Fractures: A Randomized Trial, World Journal of Surgery, 19, 388-393, May/Jun. 1995.

Shorr, R., et al., Blunt Thoracic Trauma, Annals of Surgery., 206: 200-205, Aug. 1987.

Ziegler, D, et al., The Morbidity and Mortality of Rib Fractures, The Journal of Trauma, 37: 975-979, Dec. 1994.

Beachey, W., Respiratory Care Anatomy and Physiology: Foundations for Clinical Practice, CV Mosby, St. Louis, pp. 33-40, 1998.

Haifeh, K., Basic Anatomy and Physiology of the Respiratory System and the Autonomic Nervous System. In: Timmons, B., et al., eds., Behaviorial and Psychological Approaches to Breathing Disorders, Plenum Press, New York, pp. 17-45, 1994.

Haenel, J., et al., Extrapleural Bupivacaine for Amelioration of Multiple Rib Fracture Pain, The Journal of Trauma, 38: 22-27, Jan. 1995.

Campbell, D., Trauma to the Chest Wall, Lung, and Major Airways, Seminars in Thoracic and Cardiovascular Surgery, 4: 234-240, 1992.

Richardson, J., et al., Selective Management of Flail Chest and Pulmonary Contusion, Annals of Surgery, 196, 481-487, Oct. 1982.

Sariego, J., et al., Predictors of Pulmonary Complications in Blunt Chest Trauma, Int. Surg., 78: 320-323, 1993.

Caillot, J., et al., Thoracic Trauma. In: Cavina, E., et al, eds., European Course Trauma Care, website, http://www-cdu.dc.med.unipi.it/ectc/indexectc.htm, last update May 7, 2001, 7 pages.

McRitchie, D., et al., Pneumonia in Patients with Multiple Trauma, Clinics in Chest Medicine, 16: 135-146, Mar. 1995.

Case, S., et al., Adult Respiratory Distress Syndrome: A Deadly Complication of Trauma, Focus on Critical Care, 19: 116-121, Apr. 1992.

Mathewson, H., Preventing Postraumatic Pneumonia, CRNA: The Clinical Forum for Nurse Anesthetists, 6: 114-117, Aug. 1995.

Von Rueden, K., et al., Pulmonary Dysfunction Related to Immobility in the Trauma Patient, AACN Clinical Issues, 6: 212-228, May 1995.

Pape, H-C., et al., The Effect of Kinetic Positioning on Lung Function and Pulmonary Haemodynamics in Posttraumatic ARDS: A Clinical Study, Injury, 25: 51-57, 1994.

Brower, R., et al., Ventilation with Lower Tidal Volumes as Compared with Traditional Tidal Volumes for Acute Lung Injury and the Acute Respiratory Distress Syndrome, The New England Journal of Medicine, 342: 1301-1308, May 4, 2000.

Torbin, M., Principles and Practice of Mechanical Ventilation, McGraw-Hill, New York, 411-425, 1994.

Lain, D., et al., Pressure Control Inverse Ratio Ventilation as a Method to Reduce Peak Inspiratory Pressure and Provide Adequate Ventilation and Oxygenation, Chest, 95: 1081-1088, May 1989.

Tharratt, R., et al., Pressure Controlled Inverse Ratio Ventilation in Severe Adult Respiratory Failure, Chest, 94: 755-762, Oct. 1988.

Marcy, T., et al., Inverse Ratio Ventilation in ARDS, Chest, 100: 494-504, Aug. 1991.

IP-Yam, P., et al., Combined High-frequency Ventilation (CHFV) in the Treatment of Acute Lung Injury—A Case Report, Annals Academy of Medicine, 27: 437-441, May 1998.

Ihra, G., et al., High-frequency Ventilation for Management of Respiratory Complications after Trauma and Major Orthopaedic Surgery, Anaesthesia, 53 (suppl. 2): 1-2, Apr. 1998.

Jawan, B., et al., Aspiration and Transtracheal Jet Ventilation with Different Pressures and Depts of Chest Compression, Critical Care Medicine, 27: 142-145, 1999.

Campbell, D., et al., Nitric Oxide and High Frequency Jet Ventilation in a Patient with Bilateral Bronchopleural Fistulae and ARDS, Canadian Journal of Anesthesia, 47: 53-57, 2000.

Weis, C., et al., Liquid-Assisted Ventilation: Physiology and Clinical Application, Annals of Medicine, 29: 509-517, 1997.

Dittman, M., et al, A Rationale for Epidural Analgesia in the Treatment of Multiple Ribfractures, Intensive Care Medicine, 4: 193-197, 1978.

O'Kelly, E, et al., Continuous Pain Relief for Multiple Fractured Ribs, British Journal of Anaesthia, 53: 989-991, 1981.

Abouhatem, R., et al., Thoracic Epidural Analgesia in the Treatment of Rib Fractures, Acta Anaesthesiol Belg., 35 (suppl.): 271-275, 1984.

Worthley, L., Thoracic Epidural in the Management of Chest Trauma, Intensive Care Medicine, 11: 312-315, 1985.

Rocco, A, et al., Intrapleural Administration of Local Anesthetics for Pain Relief in Patients with Multiple Rib Fractures, Preliminary Report, Regional Anesthesia, 12: 10-14, Jan.-Mar. 1987.

De Andres, J., et al., Predictors of Patient Satisfaction with Regional Anesthesia, Regional Anesthesia., 20: 498-505, Nov.-Dec. 1995.

Short, K., et al., Evaluation of Intrapleural Analgesia in the Management of Blunt Traumatic Chest Wall Pain: A Clinical Trial, The American Surgeon, 6: 488-493, Jun. 1996.

Clarke, K. Effective Pain Relief with Intrapleural Analgesia, Nursing Times, 95: 49-50, Mar. 24, 1999.

Wu, C., et al., Thoracic Epidural Analgesia versus Intravenous Patient-Controlled Analgesia for the Treatment of Rib Fracture Pain after Motor Vehicle Crash, The Journal of Trauma, 47: 564-567, Sep. 1999.

Siegel, J., et al., A Quantitative Method for Cost Reimbursement and Length of Stay Quality Assurance in Multiple Trauma Patients, The Journal of Trauma, 37: 928-937, Dec. 1994.

Roumen, R., et al., Scoring Systems and Blood Lactate Concentrations in Relation to the Development of Adult Respiratory Distress Syndrome and Multiple Organ Failure in Severely Traumatized Patients, The Journal of Trauma, 35: 349-355, Sep. 1993.

Honick, D., et al., Fractures, Rib, online serial, eMed J, Feb. 17, 2001, vol. 2, No. 2, http://www.emedicine.com/emerg/topic204.htm, Accessed Jun. 1, 2001, 6 pages.

Caillot, J., et al., Thoracic Trauma. In: Cavina, E., et al, eds., European Course Trauma Care (ECTC), website, http://www-cdu.dc.med.unipi.it/ectc/indexectc.htm, Accessed Jun. 20, 2001, 9 pages.

* cited by examiner

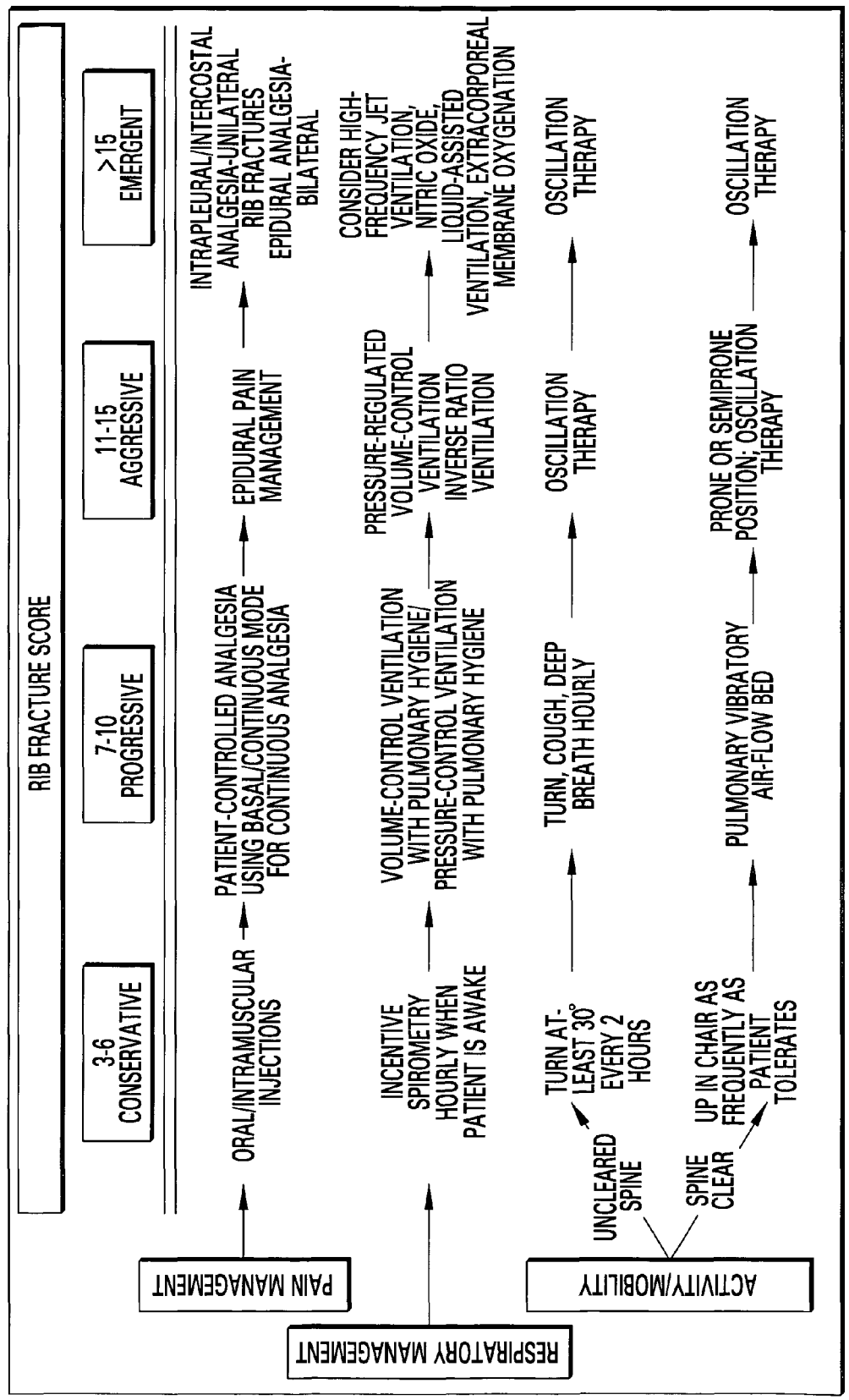

RIB FRACTURE SCORE AND PROTOCOL

CROSS-REFERENCE TO RELATED APPLICATIONS

This application claims the benefit of U.S. Provisional Application No. 60/405,579 filed Aug. 23, 2002, the disclosure of which is incorporated herein by reference.

STATEMENT REGARDING FEDERALLY SPONSORED RESEARCH OR DEVELOPMENT

Not applicable.

BACKGROUND OF THE INVENTION

1. Field of the Invention

The present invention relates to a scoring system for evaluating rib fracture trauma patients and a related protocol for utilizing the scoring system to make decisions on patient treatment.

2. Brief Description of the Related Art

Rib fractures, which account for more than half of thoracic injuries due to nonpenetrating trauma, are the most common blunt chest injury in adults. Motor vehicle crashes are the most common mechanism [1]. Significant morbidity and mortality that occur soon after multiple rib fractures are related to the underlying visceral injury, such as the degree of pulmonary contusion, the presence of hemopneumonthoraces, or injury of the aorta [2]. Other complications that can occur include hemorrhage, flail chest, atelectasis, pneumonia, respiratory failure, and death [1, 3].

Although head injury is the most common cause of death due to traumatic injury, thoracic trauma accounts for 25% of such deaths [2, 4]. Ziegler and Argarwal [4] found that of 7,147 patients admitted to a trauma center, 711 (10%) had rib fractures. Only 6% of the 7,147 patients had isolated rib fractures; therefore, 4% (289 patients) had multiple rib fractures. Their study [4] indicated patients with 1 or 2 rib fractures had a 5% mortality rate, whereas patients with 7 or more fractures, had a 29% mortality rate. Although the study did not indicate the percentage of patients with 7 or more fractured ribs, potentially 83 (29%) of the 286 patients with multiple rib fractures could have died of their injuries. Ziegler and Argarwal concluded that rib fractures were an indicator of severity of injury.

The research leading to epidural analgesia as a standard of care for pain management for patients with multiple rib fractures suggested that the respiratory system has having a major impact on patients' recovery. During normal respiration, the rib heads rotate on their vertebral articulations while leaving the vertebral column stationary; thus the sternal ends of the ribs rise and fall while the vertebral ends remain fixed. Muscular contraction elevates only the sternal ends of the ribs, causing a mechanical motion that moves the sternal ends of the ribs up and away from the vertebral column. This action increases the anterioposterior distance between the sternum and the vertebrae and enlarges the thoracic cavity volume. This simultaneous action causes a 2-dimensional enlargement by the combined effect of the 2 movements.

The external and parasternal intercostal muscles elevate the ribs, resulting in inspiration. With the relaxation of these muscles, the ribs return to their original position, a change that decreases lung volume. Changes in thoracic pressure provide the basis for generating pressure gradients necessary for air movement into and out of the lungs. The process of breathing requires the use of both bony structures and accessory muscles. Broken ribs, particularly on both sides of the vertebrae, dramatically reduce this dual-action chest movement and thus reduce the volume of air into and out of the lung [5].

Lung capacity and volume also change with the position of the body, decreasing when a person lies down and increasing when a person stands [6]. While a person is lying down, the abdominal contents push upward against the diaphragm, causing a decrease in the expansion of the lungs. Therefore, patients on bed rest have decreased pulmonary excursion.

Rib fractures can compromise ventilation by at least 3 mechanisms: (1) pain from rib fractures can cause splinting, subsequently resulting in atelectasis and pneumonia; (2) multiple rib fractures may cause flail chest which interferes with normal costovertebral and diaphragmatic muscle excursion and results in ventilatory insufficiency; and (3) these broken ribs can become penetrating objects that cause a hemothorax or a pneumothorax. The middle ribs (ribs 4 through 9) are the most commonly injured because the structurally weakest point of the rib cage is the posterior angle [7, 8]. Lung-related morbidity of patients with multiple rib fractures ranges from 13% to 69% [2].

A fracture of the first rib is considered to be a hallmark of severe trauma. The amount of force required to fracture the first rib is tremendous and should alert healthcare providers to the possibility of other injuries, such as aortic tears, cardiac injuries, or traumatic injury of the subclavian artery and brachial plexus. Patients with a fracture of the first rib also may be at high risk for late-developing injuries and complications [9, 10]. Patients with this injury should be monitored closely and complications of the injury should be anticipated.

Recognizing the mechanisms that may compromise adequate ventilation is important when managing patients with multiple rib fractures. Inadequate ventilation results from mechanical instability and subsequent splinting of the involved side of the chest, which is unavoidable because of pain [8]. Atelectasis is characterized by collapse of lung tissue on itself, which prevents the exchange of carbon dioxide and oxygen. The loss of this functional lung tissue often results in an increase in heart rate, blood pressure, and respiratory rate. The secretions then become trapped in the collapsed lung tissue. These retained secretions support the growth of bacteria, a situation that leads to stasis pneumonia, respiratory failure and acute respiratory distress syndrome (ARDS) in critically ill patients [6]. Patients with blunt trauma should be considered at risk for secondary complications, even those with favorable trauma Scores or injury severity scores [11].

In patients with blunt chest trauma and rib or sternal fractures, pain promotes splinting and is a major factor contributing to the need for intubation. Pain associated with rib fractures can prevent proper ventilation and coughing, leading to atelectasis, retained secretions and pneumonia [12]. Durable and satisfactory analgesia can prevent atelectasis, which may result in pneumonia. Nosocomial pneumonia can be prevented in these patients by use of prevention strategies, such as early fixation of fractures, rapid mobilization, and adequate pain management [13]. Gabrem et al. [2] attribute atelectasis to increased pulmonary shunting leading to hypoxemia, which may predispose patients to respiratory failure. See FIG. 1.

As a result of nearly thirty years' research in ways to prevent death and minimize complications, from multiple rib fractures, clinical management of these patients has been the key to improving outcomes. Three patient management practices have proved significance in influencing outcomes and preventing complications in patients coming to emergency trauma centers with chest trauma: rapid mobilization, respiratory support, and proper pain management [8, 14-16].

Rapid mobilization is a key factor in successfully preventing hypoventilation and atelectasis with retained secretions, which could result in pneumonia, respiratory failure and ARDS. In a study of patients with ARDS, oscillation therapy provided by a kinetic bed was compared with conventional supine positioning. The patients who had oscillation therapy had significant improvement in lung function without hemodynamic compromise. Continuous body positioning, achieved using such methods as air therapy, prone ventilation, and oscillation might be a promising treatment in ARDS. As does prone ventilation, oscillation therapy provides a larger surface of non-dependent lung sections, a situation that promotes redistribution of blood and allows lung areas previously not being ventilated to be perfused and ventilated [17, pp188-213].

Patients with bilateral rib fractures have an increased risk for complications associated with the basic nursing care that is delivered. For example, each turn or re-positioning maneuver of a patient with bilateral rib fractures places the patient at risk of receiving further trauma. The pieces of rib that have been broken may re-locate to new tissue, thus exacerbating the previous injury. Therefore, it seems reasonable to create a method to determine which patients are in the highest risk group and to provide care that minimizes the risk of complications or exacerbation of injury.

The overall goals of mechanical ventilation for patients with multiple rib fractures are to support the respiratory system while the ribs heal and to prevent complications. If patients can be mobilized, they should be encouraged to move around to maintain homeostasis in their lungs. Although mechanical ventilation may be required as supportive therapy, the prevalence of complications increases with the use of invasive therapy, and the potential for complications such as pneumonia also increases [13, 15].

Incentive spirometry therapy is a valuable tool in postoperative patients. It can also be successful with patients with multiple rib fractures. However, the patients experience significant pain with increased expiratory volumes, so adequate pain control is paramount to the success of this conservative treatment.

If mechanical ventilation is required, decisions about the mode of ventilation become important. Because ARDS is an oxygenation problem, modes that support the exchange of oxygen at the cellular level are indicated. Assist-control or volume-control mode ventilation is used for patients who have a weak respiratory effort, such as patients who are hypoventilating because of multiple rib fractures. This mode is a comfortable one that provides complete mechanical support, but it is not a weaning mode. Pressure-control ventilation has the advantage of limiting pressure, therefore it decreases the risk of barotraumas, but it does not guarantee a baseline tidal volume [17]. Pressure-control ventilation may become increasingly popular as a result of the first major advancement in ARDS in more than 30 years, made in 1999. Investigators [18] found that smaller ventilator breaths or a decrease in the tidal volume setting on the ventilator may reduce mortality in patients with ARDS.

A more aggressive mode of ventilation is pressure-regulated volume control, which adjusts the flow rate of the delivered oxygen to deliver the set tidal volume at or below the set maximum pressure. This mode is the preferred mode for patients with high airway pressures. Pressure-regulated volume control ventilation produces a guaranteed tidal volume but minimizes barotrauma [19]. The ventilator computer calculates compliance at predetermined intervals and adjusts the flow rate of the gas delivered as the patient's lung compliance changes [20].

Results of studies using inverse ratio ventilation have been reported since the 1980s [21-23]. This mode of ventilation is delivered 1 of 2 ways: (1) volume-cycled ventilation with an end-inspiratory pause, or with a slow or decelerating inspiratory flow; or (2) pressure-controlled ventilation applied with a long inspiratory time. Use of inverse ratio ventilation requires that the patient be sedated to prevent fighting the ventilator. This mode of ventilation can cause excessive gas trapping, and close monitoring is required to determine if any adverse hemodynamic effects occur [24].

Although some of the emergent modes of ventilation are experimental, or the equipment may not be readily available in all community hospitals, the modes should be included in any protocol designed to improve patients' outcomes and avoid complications associated with injuries sustained from trauma. These modes include high-frequency jet ventilation, combined high-frequency ventilation; high-frequency percussive ventilation; use of nitric oxide combined with high-frequency jet ventilation, liquid-assisted ventilation, and extracorporeal membrane oxygenation.

High-frequency jet ventilation can be delivered by using high respiratory rates (>60/min) to deliver small tidal volumes from a gas source of high pressure through a small-bore cannula. Combined high-frequency ventilation has been used when treatment with high-frequency jet ventilation is not successful [25]. High frequency percussive ventilation combines the delivery system of jet ventilation and the changes in lung volume of conventional ventilation [26, 27].

Use of nitric oxide combined with high-frequency jet ventilation is well established in neonatal intensive care. Only recently have case reports describing the outcomes of this therapy in adults been published. Campbell et al. [28] reported the successful simultaneous use of nitric oxide and high-frequency jet ventilation in a patient with ARDS with co-existing large bilateral bronchopleural fistulas.

Liquid-assisted ventilation offers an alternative ventilation strategy for supporting life during severe respiratory failure associated with ARDS. This technology is a simple process where inert perfluorochemical fluids are substituted for nitrogen as a medium for gas exchange. Use of these fluids reduces the surface tension in the lung that is created by the interface of gas and tissue. The perfluorochemical fluid recruits atelectatic lung, thereby increasing lung compliance and the area of gas exchange. The effect is to minimize barotrauma [27].

Extracorporeal membrane oxygenation is not a new therapy, but may be considered in an emergent situation. Unfortunately, if the facility providing care for the patient does not have extracorporeal membrane oxygenation, patients may have to be transferred to a facility with a cardiothoracic unit that has the equipment and has staff with expertise in the use of extracorporeal membrane oxygenation [24]. The transfer ideally would occur before the patient deteriorates.

The best outcomes in the care of patients with multiple rib fractures are associated with appropriate management of pain [29-32]. Although the exact mechanism is still being studied, pain management is an important factor in preventing complications in these patients. Epidural analgesia is becoming a standard of care [7].

In a randomized, experimental, prospective study of 100 patients requiring mechanical ventilation because of multiple rib fractures, Dittman et al. [28] concluded that effective analgesia led to an increase in the midposition tidal volume and opening of more alveoli. The control group was treated with mechanical ventilation, whereas the experimental group was allowed to breathe spontaneously with thoracic epidural analgesia for pain management. The specific outcome measures were functional residual capacity, dynamic lung compliance, vital capacity, airway resistance and $PaO_2$. The experimental group experienced a uniform rise in dynamic lung compliance, vital capacity, and functional residual capacity; a reduction in airway resistance and an increase in $PaO_2$ ($P<0.001$). The control group had an average stay in the intensive care unit of 9.8 days, compared with 4.5 days for the experimental group. Overall, epidural analgesia encouraged a favorable outcome because it enabled patients to cough effectively.

O'Kelly & Garry [29] concluded that pain from fractured ribs causes a reduction in respiratory excursion which increases the ventilation-perfusion mismatch and is the principal problem in a patient with fractured ribs. In their case report, a patient treated with nerve blocks using an intercostal injection with the aid of Tuohy needle experienced total pain relief for 8 hours. The catheter provided a method for continuous delivery of an analgesic agent across several intercostal segments of the thorax. When used for a few hours, epidural anesthetics were extremely effective in controlling pain and in enabling patients to participate in aggressive pulmonary toilet routines [9].

Abouhatem et al. [30] hypothesized that efficient pain relief with continuous thoracic epidural analgesia allowed good physiotherapy management without central sedation and impairment of the cough reflex, thus preventing pulmonary atelectasis and infection. Their hypothesis was supported in a sample of 19 patients with an average of 5 rib fractures. Worthley [31] also reported that pain relief with epidural analgesia was dramatic and was not associated with sedation. During a 6-year period, 161 patients with chest trauma were treated with thoracic epidural analgesia induced by using bupivacaine 0.5% with adrenaline 1/200000. The group had an increase in mean vital capacity from 494 (SD, 300) mL before analgesia to 1130 (SD, 199) mL after analgesia. They concluded that as a result of proper thoracic epidural pain management, patients were more alert and cooperative and thus able to participate in increased activities such as turning, getting up, and physiotherapy.

Rocco et al. [32] compared continuous versus intermittent intrapleural administration of bupivacaine for pain relief in patients with multiple rib fractures. Six patients received doses intermittently, whereas a second group of 3 patients received an initial intrapleural injection of 20 ml of 0.5% bupivacaine and then a continuous infusion of 0.25% or 0.5% bupivacaine at a rate of 5 to 10 mL/hour. Outcome measures for the intermittent dosage group were arterial blood gas pH ($P<0.001$), $PaCO_2$ ($P<0.01$) and $PaO_2$ ($P<0.001$) before and after injection. The outcome measures for the continuous infusion group were peak mean venous blood levels of bupivacaine between 1.1 and 2.38 μg/mL. Adequacy of analgesia was measured as unilateral anesthesia to pinprick from T2 to T10. Although statistical analysis was not presented for between-group differences, Rocco et al. concluded that effective pain relief could be provided with either intermittent or continuous intrapleural analgesia.

More recent research [33-36] supports the earlier findings of the necessity to adequately control pain in patients With multiple rib fractures. Clarke [35] argues that the use of intrapleural catheters for pain relief should be a widespread practice.

Optimally, if rapid mobilization, respiratory support, and pain management were simultaneously used in a systematic method, healthcare providers would be able to define the appropriate level of care for patients with multiple rib fractures. This level of care would encompass preventive care, anticipatory management, and emergent crisis care. Ultimately, delivery of the appropriate level of care delivered immediately would speed up patients' recovery.

Siegal et al. [37] studied the cost of care of patients with multiple trauma. They found that the Injury Severity Score was a poor predictor of the use of resources. Instead, the most common variable that explained more than 80% of the variability in cost was the length of stay. The most common complications involved the respiratory system. Therefore, if the most common complication can be closely managed, the length of stay theoretically should decrease, along with the cost associated with that stay.

The lungs become less elastic or they lose compliance as a result of the normal aging process. The number of alveoli and small blood vessels around the lungs diminishes. The vertebrae in the spine become compressed, causing the disc spaces to be smaller, reducing chest volume. The diaphragm and the intercostal muscles also weaken with age. These changes result in decreased lung expansion. Therefore, the lungs take in less oxygen and exhale less carbon dioxide. Overall lung function is decreased. These anatomical changes alone contribute to a vulnerability to pneumonia and bronchitis [38].

A lower threshold for admission of the elderly with isolated rib fractures may be warranted because of the higher incidence of hypoventilation, hypercapnea, atelectasis, and pneumonia [12]. The age of the patient seems to be pertinent data to include in the development of a protocol for management of patient with multiple rib fractures.

Ziegler & Argarwal [4] studied patients' outcomes after multiple rib fractures. They documented a significant correlation between mortality and increases in the number of ribs fractured. They hypothesized that most patients with multiple rib fractures will have associated injuries and proposed that as the number of rib fractures increases, so will the Injury Severity Score and mortality. Ziegler & Argarwal [4] also predicted that one third of patients will have pulmonary complications, one third will have a hemothorax or pneumothorax, and one third will require transitional or extended care.

BRIEF SUMMARY OF THE INVENTION

The present invention is directed to the care of patients with multiple rib fractures. In the present invention a score and protocol is applied to the treatment of the rib fracture trauma patient by selecting the appropriate form of rapid mobilization, respiratory support, and proper pain management will result in speedy recovery, as measured by length of stay in the intensive care unit and the hospital.

BRIEF DESCRIPTION OF THE SEVERAL VIEWS OF THE DRAWINGS

FIG. 2 is a diagram of the protocol of the present invention for management of pain, respiratory care and mobility in patients with multiple rib fractures.

DETAILED DESCRIPTION OF THE INVENTION

Figure 1:
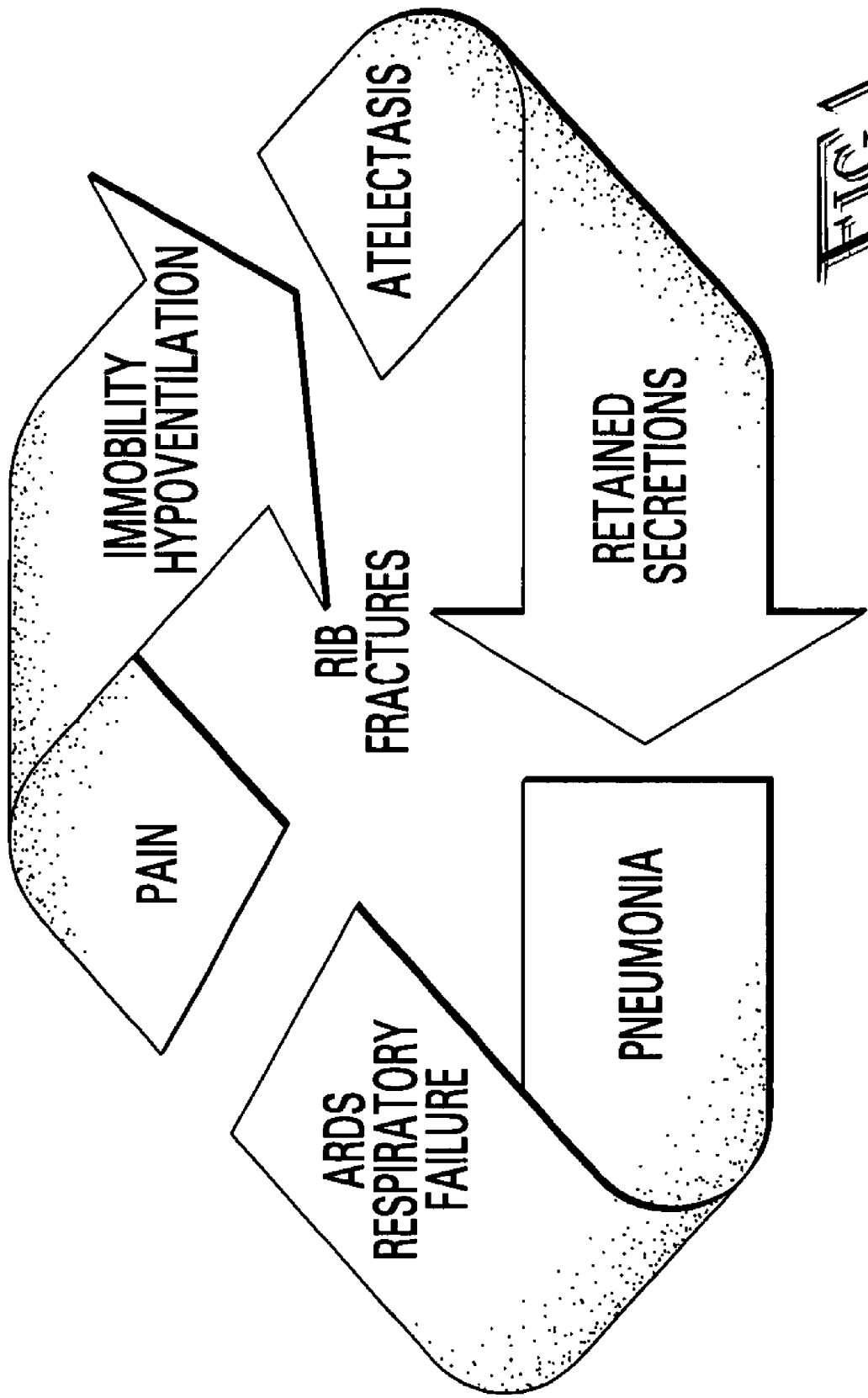
FIG. 1 is a block diagram of a model of the progression of respiratory failure/ARDS development related to pain associated with multiple rib fractures.

On the basis of the Ziegler and Argarwal data previously mentioned and the finding of other investigators, the protocol of the present invention was developed for a quality improvement project in a 10-bed trauma unit in a community hospital in the Midwestern United States.

The information obtained from the project was used to develop a formula for determining which patients are at highest risk and thus which level of care is indicated. The levels of care are conservative, progressive, aggressive, and emergent. A review of literature led to the inclusion of 3 major components of management in the protocol: pain control, respiratory support, and rapid mobilization of the patient.

Roumen et al. [38] found that scoring systems directly grading the injury severity of groups of trauma patients have predictive value for late and remote complications, such as ARDS and multiple organ failure, whereas scoring systems that grade the physiologic response to trauma have no predictive value but are related to mortality. For this reason, the Injury Severity Score was not selected for use in this protocol. Rather, looking specifically at the number of ribs fractured and differentiating unilateral versus bilateral injury seemed prudent.

When this protocol is followed, specific care should be implemented in adult trauma patients with chest injuries with a rib fracture score greater than 6. The simple formula shown in Table 1 following can be used to ascertain the rib fracture score: Rib Fracture Score=number of Breaks (1 rib broken twice is 2 breaks) multiplied by the number of Sides the injury occurs on, (unilateral is ×1, bilateral is ×2) plus an Age Factor based on the age of the patient. The age factor is a calculation to accommodate for the increased risk of complications from injuries in the elderly [12].

TABLE 1

| Rib Fracture Score = (Breaks × Sides) + Age Factor | |
|---|---|
| Breaks | Number of fractures |
| Sides | Unilateral = 1, bilateral = 2 |
| Age Factor | |
| 0 | If <50 years old |
| 1 | If 51–60 years old |
| 2 | If 61–70 years old |
| 3 | If 71–80 years old |
| 4 | If >80 years old |

As shown in FIG. 2, an increasingly progressive protocol is based on the Rib Fracture Score as a decision-making tool to provide adequate pain control, minimize complications, and to promote faster recovery from rib injuries in the expensive environment of intensive care units. The protocol suggests conservative, progressive, aggressive or emergent methods as shown in FIG. 2 for pain management, respiratory management and activity/mobility depending on the Rib Fracture Score. Conservative methods are suggested for a Rib Fracture Score of 3-6, progressive methods for a score of 7-10, aggressive methods for a score of 11-15 and emergent methods for a score greater than 15.

The present invention has been described with reference to certain preferred and alternative embodiments that are intended to be exemplary only and not limiting to the full scope of the present invention as set forth in the appended claims.

REFERENCES

1. Honick D, Sinert R. Fractures, rib. In: *eMed J* [online serial]. Feb. 17, 2001, vol. 2, No. 2. Available at: http://www.emedicine.com/emerg/topic 204.htm. Accessed Jun. 1, 2001.
2. Gabram S G, Schwartz R J, Jacobs L M, et al. Clinical management of blunt trauma patients with unilateral rib fractures: A randomized trial. *World J Surg.* 1995; 19:388-393.
3. Shorr R M, Crittenden M, Indeck M C, Hartunian S L, Rodriguez A. Blunt thoracic trauma: analysis of 515 patients. *Ann Surg.* 1987; 206:200-205.
4. Ziegler D W, Agarwal N N. The morbidity and mortality of rib fractures. *J Trauma.* 1994; 37:975-979.
5. Beachey W. *Respiratory Care Anatomy and Physiology: Foundations for Clinical Practice.* St. Louis, Mo.: C V Mosby; 1998:33-40.
6. Naifeh K. Basic anatomy and physiology of the respiratory system and the autonomic nervous system. In: Timmons B, Ley R, eds. *Behavioral and Psychological Approaches to Breathing Disorders.* New York, N.Y.: Plenum Press; 1994:17-45.
7. Haenel J B, Moore F A, Moore E E, Sauaia A, Read R A, Burch J M. Extrapleural bupivacaine for amelioration of multiple rib fracture pain. *J Trauma.* 1995; 38:22-27.
8. Campbell D B. Trauma to the chest wall, lung, and major airways. *Semin Thorac Cardiovasc Surg.* 1992; 4:234-240.
9. Richardson J D, Adams L, Flint L M. Selective management of flailed chest and pulmonary contusion. *Ann Surg.* 1981:196:481-487.
10. Sariego J, Brown J, Matsumoto T, Kerstein M. Predictors of pulmonary complications in blunt chest trauma. *Int Surg.* 1993; 78:320-323.
11. Caillot J L, Voiglio E J, Zelnicrk P, et al. Thoracic Trauma. In: Cavina E, http://www-edu.dc.med.unipi.it/ectc/indexectc.htm. Accessed Jun. 20, 2001.
12. McRitchie D I, Matthews J M, Fink M P. Pneumonia in patients with multiple trauma. *Clin Chest Med.* 1995; 16:135-146.
13. Case S C, Sabo C E. Adult respiratory distress syndrome: A deadly complication of trauma. *Focus Crit Care.* 1992; 19:116-121.
14. Mathewson H S. Preventing posttraumatic pneumonia. CRNA 1995; 6:114-117.
15. Von Rueden K T, Harris J R. Pulmonary dysfunction related to immobility in the trauma patient. *AACN Clin. Issues.* 1995; 6:212-228.
16. Pape H, Regel G, Borghmann W, Sturm J A, Tscherne, H. The effect of kinetic positioning on lung function and pulmonary haemodynamics in posttraumatic ARDS: A clinical study. *Injury* 1994;25:51-57.
17. Pilbeam S. Mechanical Ventilation: *Physiological and Clinical Applications*, $3^{rd}$ ed. Philadelphia: Mosby-Year Book; 1998.
18. Ventilation with lower tidal volumes as compared with traditional tidal volumes for acute lung injury and the acute respiratory distress syndrome. *N Engl. J Med.* 2000; 342: 1301-1308.
19. Torbin M. *Principles and Practice of Mechanical Ventilation.* New York, N.Y.: McGraw-Hill; 1994:411-421.
20. Lain D, DiBenedetto R, Morris S L, Van Nguyen A, Causey D. Pressure control inverse ratio ventilation as a method to reduce peak inspiratory pressure and provide adequate ventilation and oxygenation. *Chest.* 1989; 5:1081-1088.

21. Tharratt R, Allen R, Albertson T. Pressure controlled inverse ratio ventilation in severe adult respiratory failure. *Chest*. 1988; 4:755-762.
22. Marcy T, Marini J. Inverse ratio ventilation in ARDS: Rationale and implementation. *Chest* 1991; 100:494-504.
23. Ip-Yam P, Allsop E, Murphy J. Combined high-frequency ventilation (CHFV) in the treatment of acute lung injury: A case report. *Ann Acad Med*. 1998; 27;437-441.
24. Ihra G, Kepka A, Schabernig C, Hieber A, Kashanipour A, Aloy A. High-frequency ventilation for management of respiratory complications after trauma and major orthopaedic surgery. *Anesthesia*. 1998; 53(suppl. 2):1-3.
25. Jawan B, Cheum H, Chong Z, Fung S, Lee J. Aspiration and transtracheal jet ventilation with different pressures and depths of chest compression. *Crit Care Med*. 1999; 27:142-145.
26. Campbell D, Steimann M, Porayko L. Nitric oxide and high frequency jet ventilation in a patient with bilateral bronchopleural fistulae and ARDS. *Can J Anesth*. 2000; 47:53-57.
27. Weis C, Wolfson M, Shaffer T. Liquid-assisted ventilation: Physiology and clinical application. *Ann Med*. 1997; 29:509-517.
28. Dittman M, Keller R, Wolff G. A rationale for epidural analgesia in the treatment of multiple rib fractures. *Intensive Care Med*. 1978; 4:193-197.
29. O'Kelly E, Garry B. Continuous pain relief for multiple rib fractured ribs. *Br J Anaesth*. 1981; 53:989-991.
30. Abouhatem R, Hendrick P, Titeca M, Guerisse P. Thoracic epidural analgesia in the treatment of rib fractures. *Acta Anaesthesiol Belg*. 1984; 35(suppl.):271-275.
31. Worthley L I. Thoracic epidural and the management of chest trauma: a study of 161 cases. *Intensive Care Med*. 1985; 11:312-315.
32. Rocco A, Reiestad E, Gudman J, et al. Intrapleural administration of local anesthetics for pain relief in patients with multiple rib fractures, preliminary report. *Reg Anesth*. 1987;12:10-12.
33. De Andres J, Valia J C, Gil A, Bolinches R. Predictors of patient satisfaction with regional anesthesia. *Reg Anesth*. 1995; 20:498-505.
34. Short K, Scheeres D, Mlaker J. Dean R. Evaluation of intrapleural analgesia in the management of blunt traumatic chest wall pain: a clinical trial. *Am Surg*. 1996; 6:488-493.
35. Clarke, K. Effective pain relief with intrapleural analgesia. *Nurs Times*. Mar. 24-30, 1999; 95:49-50.
36. Wu C, Jani N, Perkins F, Barquist E. Thoracic epidural analgesia versus intravenous patient-controlled analgesia for the treatment of rib fracture pain after motor vehicle crash. *J Trauma*. 1999; 47:563-567.
37. Seigel J H, Shafi S, Goodarzi S, Dischinger P C. A quantitative method for cost reimbursement and length of stay quality assurance in multiple trauma patients. *J Trauma*. 1994;37:928-937.
38. Roumen R, Heinz R, Schlag G, Sandtner W, Koller W, Goris J. Scoring systems and blood lactate concentrations in relation to the development of adult respiratory distress syndrome and multiple organ failure in severely traumatized patients. *J Trauma*. 1993; 35:349-355.

What is claimed is:

1. A method for the treatment of a trauma patient with multiple rib fractures, comprising,
    determining a rib fracture score derived from the number of rib fractures sustained by the patient, the number of sides on which the patient has sustained rib fractures, and the age of the patient;
    selecting treatment methodologies for the patient based on the rib fracture score; and
    treating the patient using the selected treatment methodologies.

2. The method of claim 1 wherein the rib fracture score is determined by multiplying the number of rib fractures by the number of sides on which the patient has sustained rib fractures and adding an age factor derived from the age of the patient.

3. The method of claim 2 wherein the age factor is 0 if the patient is less than 50 years old, 1 if the patient is 51 to 60 years old, 2 if the patient is 61 to 70 years old, 3 if the patient is 71 to 80 years old, and 4 if the patient is greater than 80 years old.

4. The method of claim 3 wherein the treatment methodologies are selected from categories of increasingly aggressive treatment depending on the rib fracture score.

5. The method of claim 4 wherein the treatment methodologies are conservative if the rib fracture score is 3 to 6, progressive if the rib fracture score is 7 to 10, aggressive if the rib fracture score is 11 to 15, and emergent if the score is greater than 15.

6. The method of claim 5 wherein the treatment methodologies are directed to pain management, respiratory management and activity/motility of the patient.

* * * * *